United States Patent [19]

Weiss et al.

[11] 4,299,239

[45] Nov. 10, 1981

[54] EPICARDIAL HEART LEAD ASSEMBLY

[75] Inventors: Lee E. Weiss, Pittsburgh; Michael J. Dalton, Murrysville, both of Pa.

[73] Assignee: Intermedics, Inc., Freeport, Tex.

[21] Appl. No.: 9,215

[22] Filed: Feb. 5, 1979

[51] Int. Cl.³ .............................................. A61N 1/04
[52] U.S. Cl. ................................. 128/785; 128/419 P
[58] Field of Search ............... 128/639, 642, 783, 784, 128/785, 790, 419 P

[56] References Cited

U.S. PATENT DOCUMENTS

| | | | |
|---|---|---|---|
| 3,737,579 | 4/1971 | Bolduc | 128/785 |
| 3,827,428 | 12/1972 | Hon et al. | 128/642 |
| 3,835,864 | 9/1974 | Rasor et al. | 128/785 |
| 3,875,947 | 2/1974 | Jula et al. | 128/785 |
| 3,974,834 | 4/1975 | Kane | 128/785 |
| 3,976,082 | 2/1975 | Schmitt | 128/785 |
| 4,010,758 | 9/1975 | Rockland et al. | 128/785 |
| 4,066,085 | 5/1976 | Hess | 128/785 |
| 4,136,701 | 1/1979 | Barton et al. | 128/785 |

FOREIGN PATENT DOCUMENTS

| | | | |
|---|---|---|---|
| 2539553 | 3/1977 | Fed. Rep. of Germany | 128/785 |
| 1316072 | 5/1973 | United Kingdom | 128/642 |

Primary Examiner—William E. Kamm
Attorney, Agent, or Firm—Bard & Groves

[57] ABSTRACT

An epicardial lead with an insertion assembly for attaching same into good stimulating contact with the heart wall, the lead having movable fixation means for fixing the distal electrode head to the heart wall in combination with a stimulating probe electrode for delivering stimulus signals to the heart. The fixation element is preferably of a corkscrew configuration, oriented normal to the lead axis, and is normally contained within an enclosed electrode chamber. The insertion assembly provides means for releasably holding the electrode head while screwing the fixation member into the epicardial wall. Since the fixation member is free to move with respect to the electrode head, the lead can remain free to be hooked to an external pacer during the fixation step. In operation, a separate stimulus probe is inserted in at various points of the epicardium for testing of threshold and when a good threshold is attained, the lead is then fixed to the heart by screwing the fixation member while maintaining the probe electrode in its desired position.

1 Claim, 12 Drawing Figures

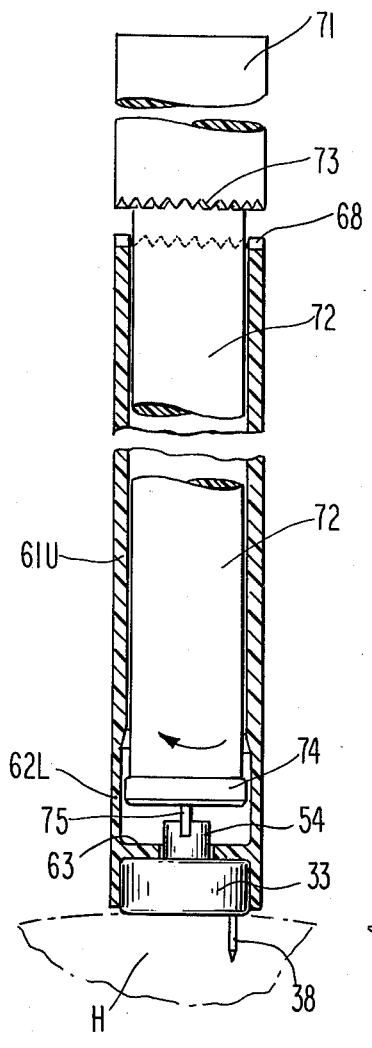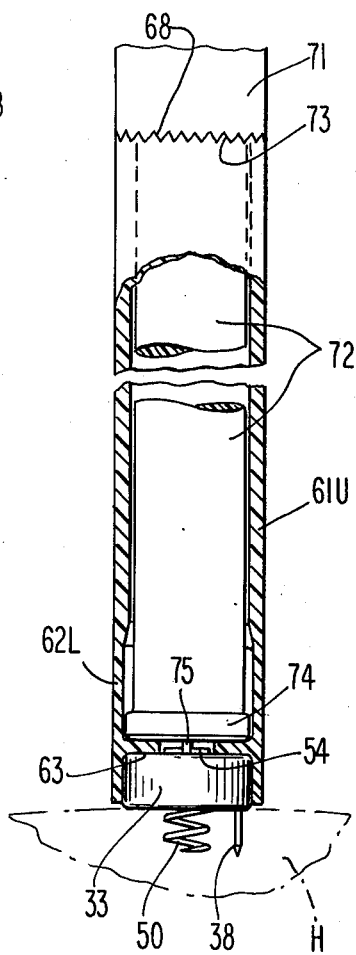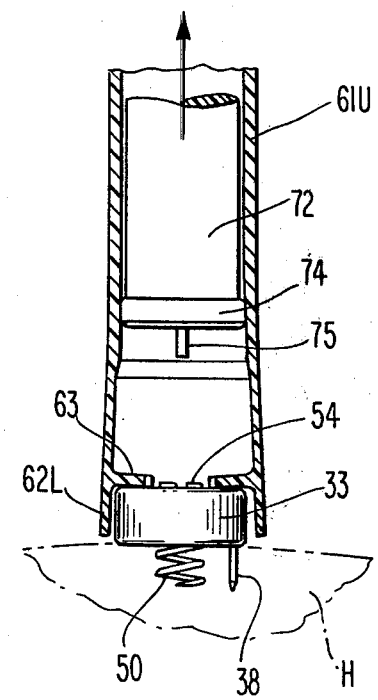
*Fig.5A*  *Fig.5B*  *Fig.5C*

EPICARDIAL HEART LEAD ASSEMBLY

CROSS REFERENCE TO RELATED APPLICATION

Reference is made to the application for EPICARDIAL HEART LEAD AND ASSEMBLY AND METHOD FOR OPTIMAL FIXATION OF SAME FOR CARDIAC PACING, invention of Lee Weiss, filed concurrently herewith, Ser. No. 8,991.

BACKGROUND OF THE INVENTION

This invention lies in the area of leads for delivering electrical signals to body organs and, more particularly, epicardial leads for use in cardiac pacing systems and having means for fixation to the heart wall.

In cardiac pacing systems it is known that in a certain proportion of patients it is desirable to utilize an epicardial lead, to ensure good fixation and permanent engagement of the lead to the heart wall. This is the case primarily because in a certain number of patients proper lead fixation cannot be achieved with endocardial leads, or catheters, and in order to obtain fixation with a desirable threshold an epicardial type lead is required. A number of epicardial leads are presently available for use with pacing systems, the most common forms involving a screw type element at the distal end of the lead, which element serves both as the stimulus electrode and as the fixation member. In these prior art arrangements, the fixation member is integrally connected to the lead, and while it may be flexible so as to facilitate engagement with the heart wall, the fixation member generally is not movable relative to the lead itself. This prior art feature places certain constraints upon lead design, as well as upon the design of insertion tools used for actually fixing the epicardial lead to the patient's heart. Examples of prior art epicardial leads and insertion assemblies include those disclosed in U.S. Pat. Nos. 4,007,745, 3,737,579 and 3,875,947.

There are a number of characteristics of the heretofore available epicardial leads and systems for inserting same which are considered to be undesirable and which need improvement. For example, the fixation means, which generally is a screw or "corkscrew" type element is fixed to the lead in such a manner that rotation of the corkscrew element into the heart wall involves rotation of the remainder of the lead itself, necessitating special insertion tools for avoiding placing torque on the remainder of the lead. Additionally, there is no restraint upon the ability of the operator to continue to turn the corkscrew element after it has been fully threaded into the heart wall. It is well known that if the corkscrew element is turned after it has been fully extended into the heart wall there is resulting trauma to the myocardial tissue, and fibrosis. Further, it is unpractical to use a screw type element to probe for a proper position which gives a desirable threshold, since repeated engagement and disengagement of such a corkscrew type element causes unwanted if not intolerable trauma to the myocardial tissue. If a separate probe element is used to determine a position for obtaining a good threshold placement, this is still a very unsatisfactory technique since the probe element must be removed and the corkscrew element inserted. Generally the results are not optimal, both because it is difficult to reinsert the corkscrew element at the same place as the probe had been inserted, and because the surface characteristics (and thus the threshold characteristics) of the corkscrew element are different from the probe which had been used.

In other prior art leads, an attempt is made to screw into the heart tissue axially, by somehow applying rotational force from the proximal end of the lead. See, for example, U.S. Pat. Nos. 3,827,428 and 3,974,834.

There is thus a substantial need in cardiac pacing systems for a means and a method for efficient and reliable fixation of an epicardial lead, providing for optimum contact electrode placement and maximum secure fixation.

SUMMARY OF THE INVENTION

It is a first object of this invention to provide a lead having a separate fixation means designed to be operated so as to avoid trauma to the myocardial tissue at the point of pacing, in combination with a separate stimulating electrode, the stimulating electrode being designed both for optimum delivery of stimulating pulses to the heart and for initial probing to determine a good site for permanent implantation. It is a second object of this invention to provide a tool assembly for efficient and reliable insertion of a sutureless epicardial electrode.

It is another object of this invention to provide a lead with electrode means for probing the heart to determine a good site for stimulating with low threshold and then providing good fixation without withdrawing the probe element which remains as the stimulus electrode.

It is another object of this invention to provide a form of electrode for a pacing lead, and an accompanying insertion tool assembly for providing good sutureless placement of an epicardial lead.

It is a further object of this invention to provide means for reliable coupling and decoupling of a lead to a heart wall or to the wall of another body organ, including an insertion tool assembly to be used in combination with the lead which remains fixed in the heart wall.

It is another object of this invention to provide means for achieving optimal fixation of an epicardial lead by inserting a corkscrew element a predetermined amount into the heart wall.

It is another object of this invention to provide a method for efficiently probing a patient's heart to determine a position for fixing a stimulating electrode, and for achieving optimal fixation of the stimulating electrode once such good position has been found.

It is another object of this invention to provide a lead with fixation means at its distal end, which fixation means are directly manipulable by an insertion tool applied to such distal end.

In accordance with the above and other objectives as are discussed hereinbelow, there is provided an epicardial heart lead having fixation means, preferably including a screw type element, which is movable relative to an electrode chamber at the distal end of the lead, such that the fixation means can be attached to the heart wall while the remainder of the lead is free and unaffected by the fixation operation. The fixation element is normally retained within the electrode head by a mesh-reinforced membrane. The lead comprises, at its distal end, a probe element which is connected to act as a stimulating electrode, which probe element is mechanically independent of the fixation element but which is positioned such that engagement of the heart wall by the fixation element secures the probe electrode at the desired position in the patient's heart. For operation in conjunction with the lead there is provided an insertion assembly including means for rotating the fixation element and means for releasing the lead from the insertion assembly after proper fixation has been achieved. The preferred embodiment preferably also includes means for constraining further movement of the fixation element after it has been fully moved out of its housing and into the myocardium, so as to minimize trauma and fibrosis resulting from the fixation.

BRIEF DESCRIPTION OF THE DRAWINGS

FIG. 5A is a detailed view showing the engagement of the insertion tool assembly with the electrode head at the start of the procedure of fixing the electrode to the heart wall;

FIG. 5B is a detailed view showing the relation of the insertion tool assembly to the electrode head at the time of complete insertion of the fixation element into the heart wall; and FIG. 5C is a detailed view showing the relation of the insertion tool assembly to the electrode head after fixation has been completed and after withdrawal of the screwdriver tool within the insertion tool for release of the electrode head.

DESCRIPTION OF THE PREFERRED EMBODIMENTS

Figure 1:
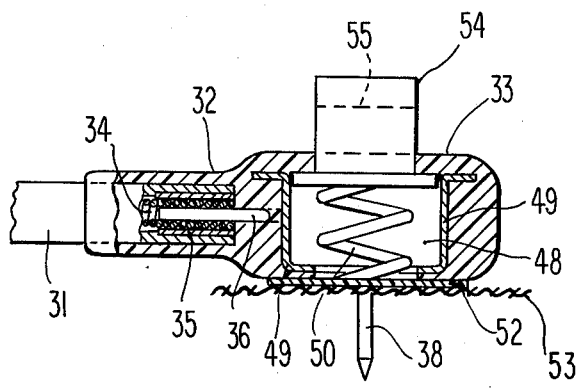
FIG. 1 is a side view of the distal electrode head of the lead of this invention, illustrating in detail the fixation and probe elements.

Referring now to FIG. 1, there is shown a view of the electrode head portion of the lead of this invention. The main length of the lead is designated as 31, which is a conventional insulating body-compatible casing embedding the conductor 34 (for a unipolar embodiment) or conductors (for a bipolar embodiment) which connect the proximal end (not shown) to the distal electrode. The conductors are suitably helical and made of a standard conductive material. The proximal end may comprise any conventional arrangement for connection to the output of a cardiac pacer as used in cardiac pacing systems, or to another type of device for other physiological stimulating or sensing systems. The lead casing is preferably made of a medical silicone.

Figure 2:
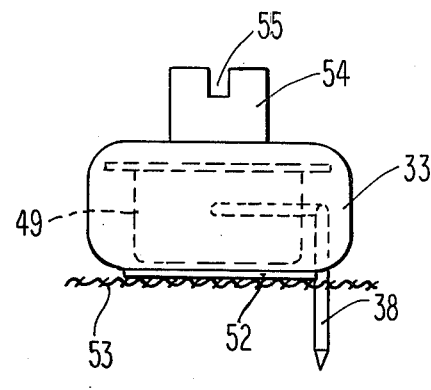
FIG. 2 is another side view of the distal electrode head, as seen from a position longitudinally distal from the end of the lead, further illustrating the desired position of the probe element and a portion of the mechanism for operating the fixation element.
Figure 3:
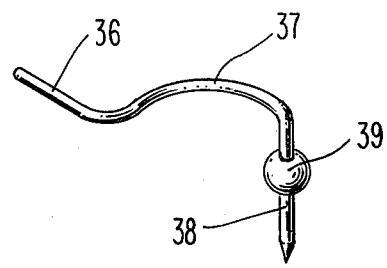
FIG. 3 is a perspective view of the probe element.

The lead casing 31 develops, at the distal end, into an enlarged lead portion 32 just proximal of the electrode head 33, both of which are formed of a suitable elastomer. In a preferred embodiment, enlarged portion 32 has a diameter of about 0.09 inch, while electrode head 33 has a diameter of about 0.440 inch. Within enlarged portion 32 the coil conductor 34 terminates within crimp sleeve 35, preferably formed of titanium, and the proximal portion 36 of probe 37 is positioned within the end of conductor 34 and in tight conductive relation thereto. As is seen by observation of FIGS. 1, 2 and FIG. 3 as well, probe 37 curves around near the perimeter of electrode head 33 and then drops downwardly, terminating in needle portion 38 which forms the actual stimulus tip for delivery of stimulus signals which have been generated in the stimulus pacer. Stimulus portion 38 is suitably a 4 mm length of 20 mil wire, pointed at the end as shown, such that it can easily penetrate or probe into the heart wall. It may also suitably include a ball, or sphere 39, as seen in FIG. 3, to modify the stimulus electrode geometry for the purpose of enhancing the electric field, whereby better threshold is obtained. The probe portion 38 is displaced from the proximal portion 36 so as to make it less susceptible to be dislodged if the main portion 31 of the lead is moved.

Still referring to FIG. 1 there is shown an inner chamber 48 defined by chamber housing 49, preferably made of titanium. Chamber 48 houses screw 50 which, in the preferred embodiment, constitutes the fixation member of the lead of this invention. Screw 50 is suitably made of MP 35N alloy, providing spring steel characteristics. Screw 50 is attached at its top to an electrode cap 54 which penetrates upward through the top surface of electrode lead head 33. Cap 54 fits loosely through the surface of head 33, such that it can be rotated by application of a screwdriver type tool to the slot 55 in cap 54, which slot is illustrated in FIG. 2. Before use, screw 50 is contained at the bottom by a membrane 52 which is secured to the bottom surface of head 33 by a suitable medical adhesive. Membrane 52 is suitably made of silicone reinforced with Dacron (Registered Trademark). It is of sufficient strength to prevent screw element 50 from falling through it, but is easily penetrated by the tip of screw element 50 when it is rotated. While element 50 can be screwed down and through membrane 52, the mesh within it acts to prevent further rotation of the screw element after it has advanced out of chamber 48. A Dacron (Registered Trademark) mesh 53 is suitably adhered to the bottom of membrane 52, as illustrated. Additionally, the bottom surface of electrode head 33 may be formed with a curvilinear surface which is slightly concave upward, for more optimal interfacing with the heart wall.

It is to be noted however that an important structural feature of the distal end of the lead is that the fixation member 50 is free to rotate and move with respect to the electrode head 33. Other than the membrane 52 which is specifically designed to be penetrated by the screw member 50, there is no constraint to movement of the screw member 50 within the chamber 48. Electrode cap 54 has a base plate which prevents movement of the screw element 50 out of the chamber 48 in either the upward or downward direction. Movement of member 50 is in a plane transverse to the axis of the lead, i.e., at right angles to the lead axis. Torque can be applied directly to member 50 through rotation of cap 54.

It is seen that needle probe 38 has a fixed geometrical relationship to the axis along which screw element 50 is moved. In operation, the physician who is implanting the pacer and connecting the lead to the heart wall probes with needle probe 38, testing patient threshold, until a desired stimulating location is found. At this time, the physician retains the needle 38 fully inserted into and engaging the heart wall at the desired location, and then moves fixation element 50 so as to securely engage the electrode head so as to maintain probe 38 in secure position at the point where the physician wants it. Note that element 50 and electrode cap 54 move freely relative to the electrode head 33, and at a right angle to the lead axis. By this means, the step of fixation, during which element 50 is actually screwed into the heart wall, does not affect at all the maintenance of probe 38 at the desired location. Note that the force being exerted does not tend to displace probe 38. Probe 38, being of a basically needle-like geometry, can be inserted at various points in order to find the desired threshold position, without causing any great amount of trauma to the heart wall. Also, its design is better adapted than a screw type configuration for avoiding growth of tissue around the stimulus such as reduces chronic threshold undesirably. Since the stimulating probe 38 is physically separate from the implanted screw element 50, any tissue that grows in around screw element 50 has no effect on the stimulus characteristics of the probe itself.

Figure 4A:
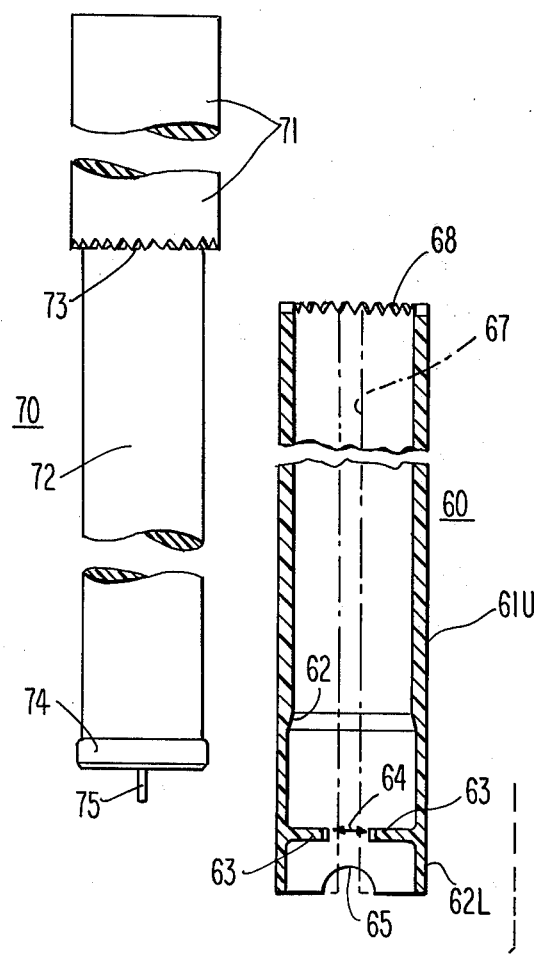
FIG. 4A is a detailed illustration of the insertion tool 60 and screw driver tool 70 comprising the insertion assembly of this invention.
Figure 4B:
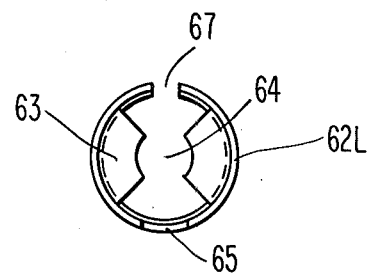
FIG. 4B is a sketch of the bottom view of the insertion tool 60.

Referring now to FIGS. 4A and 4B, there are shown views of the insertion tool 60 and screwdriver tool 70 which, in combination, comprise the insertion tool assembly of this invention. Insertion tool 60 is a generally cylindrical tube made of a suitable plastic material, having an upper portion 61U of a given inner diameter and a bottom portion 62L of a larger inner diameter relative to the upper portion. As noted at point 62, the wall thickness changes between upper portion 61U and lower portion 62L, thereby providing the change in inner diameters of the two portions. The inner diameter of portion 62L is, in the preferred embodiment, 0.436 inch, which is to be compared with the 0.440 outside diameter of the lead head. The small bottom chamber defined by walls 62L and horizontal stop elements 63 is thus of a size and form to friction capture electrode head 33. The opening 64 defined by stop elements 63 has a diameter which is slightly larger than the diameter of electrode cap 54, so that the cap can freely extend through the opening. Note that the stop elements hold cap 54 in axial alignment as it is being rotated, thus insuring proper entry of screw element 50 into the heart wall. As seen in both FIG. 4A and FIG. 4B, there is a notch 65 at the bottom of insertion tool 60, having a radius of about 0.08 inch, providing sufficient opening to accommodate enlarged lead portion 32 when the electrode head is captured by the tool 60. By this means, the main length of the lead remains outside of the tool, and is free thereof. Further, this outside length is unaffected by the fixation step. Notch 65 also can be used to guide the tool back onto the electrode head if there is need to affix the tool to the electrode a second time.

The screwdriver type tool 70 is comprised of an upper portion 71 of a first larger diameter, and a lower portion 72 of a smaller diameter. As is seen by referenced FIGS. 5A, 5B and 5C, the screwdriver tool is positioned within the insertion tool 70, the diameter of lower portion 72 being smaller than the inner diameter of portion 61U of the insertion tool. Screwdriver tool 70 is forced into the insertion tool by expanding the insertion tool at slit 67. Slit 67 is shown, in FIG. 4B, as being approximately 0.09 inch in width, but may be less, the purpose being only to allow the tool to be expanded sufficiently to fit the screwdriver tool inside of it. In any event, slit 67 is sufficiently small so that the casing 31 of the lead cannot get into it. Further, the presence of screwdriver tool 70 inside of tool 60 leaves insufficient room for putting the lead within tool 60.

Screwdriver tool 70 has at the bottom extension thereof an enlarged ring portion 74, of an outer diameter which is greater than the inner diameter of portion 61U but less than the inner diameter of portion 62L of the insertion tool. Thus, screwdriver tool 70 is normally maintained within insertion tool 60 at a position such that enlarged ring 74 is found between the stops 63 and the thickness change point 62. Extending from the very bottom end of screwdriver tool 70 is a screwdriver blade 75, adapted to interfit with the screwdriver receiving slot 55 of electrode cap 54. Although blade, or bit 75 is illustrated as a conventional screwdriver type blade, it may have an Allen-type form for easier insertion of the bit into the slot or comparable receiving receptacle 55 of electrode cap 54. Other mating forms for achieving interaction of tools 60 and 70 may also be used.

An additional feature illustrated in FIGS. 4A and 5A comprises means for restraining movement of the corkscrew element 50 once it has been fully extended down and out of the bottom of distal electrode chamber 48. This means is provided by the teeth 68 at the top of insertion tool 60 and the teeth 73 around the perimeter of screwdriver tool 70 between upper portion 71 and lower portion 72. Tool 70 is made of a predetermined length relative to tool 60, such that when the screwdriver bit 75 rests within slot 55 of electrode cap 54, teeth 73 are above matching teeth 68 by a distance comparable to the axial or longitudinal length of corkscrew element 50. As the screwdriver is rotated by the physician to screw element 50 into the heart wall, teeth 73 advance relatively toward teeth 68. When the corkscrew element 50 is fully inserted, the teeth 73 engage with teeth 68, preventing further rotation of screwdriver tool 70. By this means, the operator or physician is prevented from continuing to rotate the screw 50 after it has been fully moved out of chamber 48 and into the myocardium (designated as H). This prevents unneeded and unwanted rotation of element 50 such as would tear the heart wall and produce trauma and resulting fibrosis.

Referring now to FIGS. 5A–5C, there are shown three diagrammatic illustrations of the manner of fixing the screw element 50 into the heart H, and of then releasing the fixed electrode head 33 from the tool assembly 60, 70. In FIG. 5A, the screwdriver tool has been positioned so that it is engaging the electrode cap 54, but the corkscrew element 50 has not yet been moved through the membrane 52 and into the heart H. Note that the distal electrode head 33 is snugly friction captured within the bottom of tool 60, with the electrode cap 54 extending above stop elements 63, so that the receiving slot 55 is available to receive the screwdriver blade 75. The enlarged ring portion 74 of the screwdriver tool is within the larger inner space defined by wall 62L. As the screwdriver element is rotated, the cap 54 and the screw element 50 carried thereby are caused to rotate outward and downward from electrode head 33, thereby engaging the heart H. When the screw element 50 is fully extended out of head 33, the enlarged ring portion 74 abuts stops 63, and gear teeth 73 engage gear teeth 68. This is the condition illustrated in FIG. 5B. At this point, fixation has been achieved, and it is desired to release the electrode, leaving it securely in place attached to the heart wall. This is done by pulling up on screwdriver tool 72, so that its blade disengages from slot 55 in cap 54. At the same time, as seen in FIG. 5C, outer ring 74 comes into contact with the insertion tool wall at point 62, forcing that wall radially outward, thereby releasing electrode head 33 from its friction fit within lower wall 62L. Under these circumstances, the physician simply withdraws the insertion assembly from the electrode head, leaving the electrode firmly in position.

Referring now to FIGS. 6A-6D, there is illustrated an alternate embodiment of the insertion tool assembly of this invention which possesses certain additional advantages. As seen particularly in FIG. 6A, the insertion tool 60 has a slit 67 which is very narrow, suitably 0.015 inch. Further, it extends from the bottom longitudinally up to only about the midway point or less of the insertion tool, where it terminates in hole 85 which is designed to relieve stress. By not extending the slit the entire length of tool 60, it is more rigid at the top part and thus can be handled somewhat more effectively. Also, it is seen that the sloped portion 62 is contiguous with a longitudinally straight portion 82 which terminates in a shoulder 83, which shoulder is designed to block the ring portion 74 of the screwdriver tool so that it cannot be pulled out of tool 60. In practice, the inner diameter $R_1$ within walls 62L is suitably 0.435 inch; the diameter $R_2$ is 0.410 inch, and $R_3$ is 0.385 inch. By constructing the ring portion 74 of the screwdriver tool to be 0.425 inch in diameter, it is seen that when the screwdriver tool is pulled up to the point where ring portion 72 corresponds to radius R2, the lower walls 62L are expanded to release the electrode head. However, ring portion 72 cannot be pulled beyond the shoulders 83.

Figure 6A:
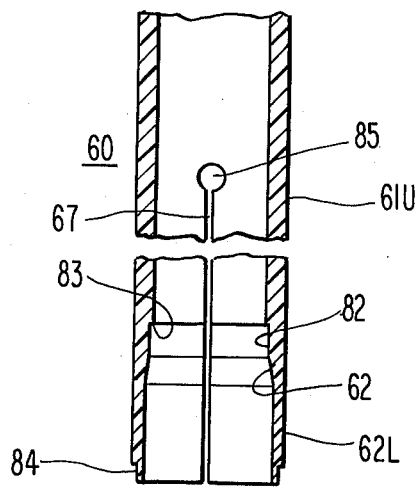
FIG. 6A is a side view of an alternate embodiment of the insertion tool 60.
Figure 6C:
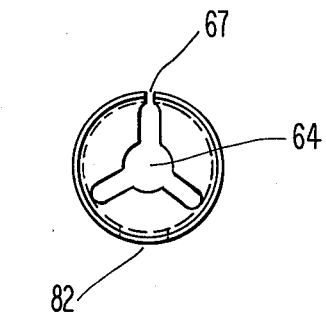
FIG. 6C is a sketch of a top view of the element 86 of FIG. 6B.
Figure 6B:
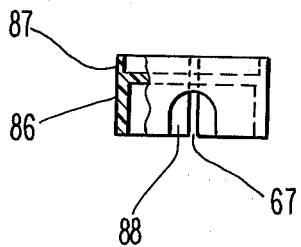
FIG. 6B is a side view, partially broken away, of a bottom portion 86 which is interfitted onto the insertion tool of FIG. 6A.

Referring to FIGS. 6A-6C, it is seen that the bottom portion of tool 60 which captures the electrode head is a separate piece 86, having upper annular portion 87 with a slightly larger inner diameter than $R_1$. Portion 87 is designed to interfit with notch 84 as seen in FIG. 6A. A somewhat enlarged notch 88 is illustrated, to provide more room for feeding the lead portion 32 outside of the insertion tool.

Figure 6D:
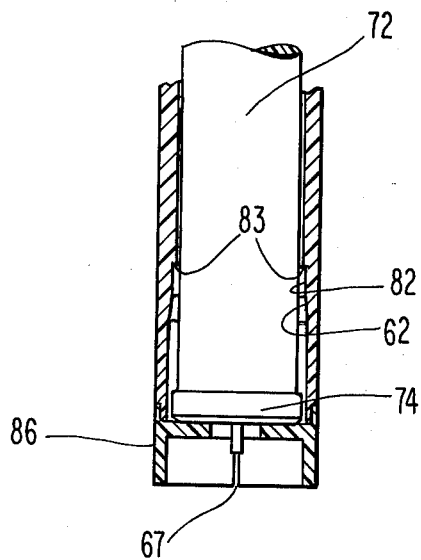
FIG. 6D is a sketch showing bottom element 86 adhered to insertion tool 60, with the screwdriver tool 70 in place within insertion tool 60.

In practice, the insertion assembly of the embodiment illustrated in FIGS. 6A-6D is fabricated by first drawing the screwdriver tool 70 up through the bottom opening of tool portion 60, until ring portion 74 is fully within portion 60. Then the bottom portion 86 is fitted into notch 84 and secured with a suitable adhesive, resulting in the assembled combination of insertion tool 60 and screwdriver tool 70, as illustrated in FIG. 6D.

There is thus shown apparatus and a method for probing the heart wall to determine a good place for obtaining optimum threshold stimulation of the heart (using conventional threshold testing means) and fixating the stimulating probe in the heart while maintaining the desired probe position, such fixating being implemented without placing any stress or torque on the remaining part of the lead. The fixation mechanism utilized is different and independent from the pacing and probing electrode, which electrode can be designed with a geometry which need not take into account any fixation requirements. The insertion apparatus utilized provides for easy and secure clamping of the electrode head for probing and fixating, and equally efficient and easy releasing of the electrode head when it has been secured to the heart wall.

Accordingly, the objects as outlined above are achieved efficiently and reliably. In the preferred design, the physician turns the distal end of the electrode 2½ turns to achieve fixation, after which further rotation is prevented. Optimal fixation is achieved because the physician knows that he must continue to rotate the fixation element until it can no longer turn. If he turns it less, it is not extended fully for optimal fixation. While the stop mechanism has been illustrated as being incorporated into the insertion tools, it can equally be designed into the head itself by putting the two sets of teeth on the bottom of cap 54 and the bottom of chamber housing 49 respectively.

While the preferred lead as illustrated comprises a separate probe 38 and fixation element 50, it is to be understood that fixation member 50 might also be utilized as a stimulus electrode, either alone or in combination with a probe element. Electrical connection may be made between conductor 34 and fixation member 50 by conventional commutating means.

We claim:

1. The combination of a lead and an insertion assembly for inserting said lead into a heart wall, comprising:
   a. a lead for delivering cardiac pacing signals, said lead having a conductor length and a distal portion comprising movable fixation means, said fixation means being mounted for movement at an angle to said conductor length and movable relative to the distal lead portion and independently of said conductor length;
   b. an insertion tool for holding said distal portion while maintaining the remainder of said lead free, said insertion tool comprising a substantially hollow cylinder having an upper portion of a first smaller inner diameter and a lower portion of a second larger inner diameter, said lower portion being adapted to friction capture said lead distal portion; and
   c. a screwdriver tool for moving said fixation means relative to said distal lead portion, and at an angle to and without moving said conductor length, said screwdriver tool being positioned within said insertion tool, said screwdriver tool having an annular element with a diameter intermediate said insertion tool upper portion inner diameter and lower portion inner diameter, whereby when said annular element is positioned in said insertion tool smaller diameter upper portion it causes outward expansion of the entire insertion tool, thereby altering the dimensions of said insertion tool and providing for release of said insertion tool from said lead distal portion.

* * * * *